United States Patent [19]
Verstreken et al.

[11] Patent Number: 5,752,772
[45] Date of Patent: May 19, 1998

[54] SENSOR ARRANGEMENT FOR TEMPERATURE MEASUREMENT

[75] Inventors: Paul Clement Verstreken, Hasselt; Jozef Theodoor Aegten, Bocholt, both of Belgium

[73] Assignee: Heraeus Electro-Nite International, N.V., Houthalen, Belgium

[21] Appl. No.: 523,967

[22] Filed: Sep. 6, 1995

[30] Foreign Application Priority Data

Sep. 21, 1994 [DE] Germany .................... 44 33 685.3

[51] Int. Cl.⁶ .............. G01K 1/10; G01K 1/12; G01K 13/12
[52] U.S. Cl. .................. 374/139; 374/157; 136/234; 73/864.59; 73/DIG. 9
[58] Field of Search ................ 374/139, 140, 374/157; 136/234; 73/DIG. 9, 864.59, 864.53, 864.51

[56] References Cited

U.S. PATENT DOCUMENTS

| | | | |
|---|---|---|---|
| 1,119,627 | 12/1914 | Mueller et al. | 374/157 |
| 1,479,750 | 1/1924 | Smith | 374/157 |
| 2,359,794 | 10/1944 | Rogers | 374/140 |
| 2,390,052 | 12/1945 | Bernstorff et al. | 374/139 |
| 3,329,308 | 7/1967 | Pool | 73/864.53 |
| 3,643,509 | 2/1972 | Surinx . | |
| 3,813,944 | 6/1974 | Ryntz, Jr., et al. . | |
| 3,844,172 | 10/1974 | Jeric | 374/157 |
| 4,112,769 | 9/1978 | Falk | 73/864.53 |
| 4,261,202 | 4/1981 | Kawamoto et al. | 374/157 |
| 4,603,590 | 8/1986 | Staats et al. | 73/DIG. 9 |
| 4,842,417 | 6/1989 | Asbjornsen | 374/139 |
| 5,037,211 | 8/1991 | Nakashima et al. | 374/139 |
| 5,069,553 | 12/1991 | Phillippi | 374/140 |

FOREIGN PATENT DOCUMENTS

| | | | |
|---|---|---|---|
| 1293478 | 12/1969 | Germany | 374/157 |
| 2225766 | 12/1972 | Germany . | |
| 20 04 819 | 2/1975 | Germany . | |
| 28 44 417 | 3/1980 | Germany . | |
| 27 30 813 | 10/1980 | Germany . | |
| 0020637 | 2/1982 | Japan | 73/864.53 |
| 0649857 | 2/1951 | United Kingdom | 374/157 |

OTHER PUBLICATIONS

Reinhard Döpp, "Bietrag zur Beurteilung der eutektischen Graphitisierung von Gusseisen durch thermische Analyse," *Giesserei* 76, 1989, Nr. 2, Jan. 23, pp.47–53.

Soviet Union (SU), A. 1326974, published Jul. 1987 (Abstract only).

*Primary Examiner*—Diego F. F. Gutierrez
*Attorney, Agent, or Firm*—Panitch Schwarze Jacobs & Nadel, P.C.

[57] ABSTRACT

A sensor arrangement for measuring the temperature of molten masses uses a receptacle having at least one strip-shaped or wire-shaped carrier and an opening on its upper side, with a thermoelement placed inside the receptacle. In order to make available a sensor arrangement for the exact determination of the liquidus temperature of molten cryolite, the receptacle is made of metal. A temperature measuring device with a sensor arrangement of this type, has at least one carrier mounted at its end facing away from the receptacle in a sleeve, the sleeve being detachably connected to a mounting device. In addition, a process for measuring the liquidus temperature of molten cryolite in a receptacle vibrates the receptacle during the cooling of the molten cryolite.

15 Claims, 2 Drawing Sheets

SENSOR ARRANGEMENT FOR TEMPERATURE MEASUREMENT

FIELD OF THE INVENTION

The invention pertains to a sensor arrangement for measurement of the temperature of molten masses, with a receptacle which has at least one strip-shaped or wire-shaped carrier and an opening on its upper side, and with a thermoelement arranged inside the receptacle. The invention also pertains to a temperature device and a process for measuring the liquidus temperature of cryolite melts.

BACKGROUND OF THE INVENTION

Sensor arrangements of this type are used, for example, for determination of the liquidus temperature of melts, wherein the cooling curve of the melt poured into the receptacle is determined. Information with regard to the composition of the melt can be obtained from the liquidus temperature. A known device of the type mentioned above for the measurement of the liquidus temperature of cryolite melts has a graphite crucible for taking samples, wherein a thermoelement is arranged. The graphite crucible is fastened to a mounting device by means of a metal rod. For taking a sample, the graphite crucible is dipped into the cryolite melt and is withdrawn from the melt with a melt volume of about 3 cm$^3$ after thermal equilibrium is reached. After that, the cooling curve is recorded and the liquidus temperature is determined therefrom. The values for the liquidus temperature obtained with this measuring device have a variation of several degrees, and are thus very inexact, so that in practice, the measurement results cannot be used reliably.

A different device for temperature measurement is known from U.S. Pat. No. 3,643,509. With the device described there, it is possible to take liquidus measurements in steel. In this regard, a thermoelement is arranged in a small, U-shaped quartz tube inside a receptacle made of quartz. The receptacle is arranged in the usual way at the tip of a measuring head and has several lateral inlet openings for the molten steel. This device is used for measurement of the bath temperature after immersion into the steel melt, and for measurement of the liquidus temperature after being withdrawn from the molten steel. Arrangements of this type cannot, as a rule, be used for melts with, for example, low heats of fusion and poor thermal conductivity, such as cryolite melts.

SUMMARY OF THE INVENTION

It is an object of the present invention to create a sensor arrangement of the type mentioned at the beginning, with which the exact measurement of the liquidus temperature of molten cryolite is made possible and which at the same time can also be economically produced. In addition, it is also an object of the invention to make available a temperature measurement device and a procedure for measurement of liquidus temperature of molten cryolite, with which measurement results can be reproducibly obtained with a high degree of accuracy.

These objects are achieved for the sensor arrangement described at the outset by constructing the receptacle of metal. A receptacle of this type has a relatively low thermal capacity and a high thermal conductivity, so that the receptacle can absorb only a very small amount of heat from the molten cryolite. In this regard, it is advantageous that the receptacle have a wall thickness of less than 0.5 mm, in particular less than 0.2 mm, and that copper is preferably used as the material for the receptacle.

When a cold arrangement is dipped into molten cryolite, the latter solidifies immediately at the components with the lower temperature. Once thermal equilibrium has been achieved, however, this solidified cryolite will melt again. This re-melting takes place most quickly in a thin-walled receptacle with high thermal conductivity, since, first of all, only a very small quantity of heat can be absorbed by the receptacle and, secondly, the receptacle is heated very quickly as a result of a high thermal conductivity.

For an exact measurement, it is advantageous that the receptacle have a corrugated surface. As a result, the surface area of the solidifying cryolite melt is increased; after the withdrawal of the sensor arrangement from the melt, the solidification first takes place in the region of this surface, and then continues evenly into the interior of the melt.

It is expedient that the thermoelement be arranged in a quartz tube, in particular in a quartz tube which is closed on one end and which has a non-oxidic protective coating. A thermoelement of that type is resistant to molten cryolite, and can be made with a small volume, so that only a very slight carrying off of heat takes place via the thermoelement. It is expedient to make the protective coating of a temperature resistant metal or non-oxidic ceramic in order to increase the resistance to the molten cryolite. For an exact recording of the cooling curve, it is advantageous that the thermoelement be arranged approximately in the center of the receptacle.

In order to ensure a secure handling of the sensor arrangement, it is expedient that the carrier(s) are made of metal wires, since the latter exhibit a high resistance with respect to the molten cryolite. In addition, it has also proven advantageous that the at least one carrier is rigidly connected with a vibrator.

In addition, it can be expedient that the inner surface of the receptacle have a roughness greater than 1.25 μm, preferably between 2.5 μm and 15 μm.

The object is achieved for a temperature measuring device with a sensor arrangement of the type described above by the at least one carrier being mounted at its end facing away from the receptacle in a sleeve, and the sleeve being detachably connected to a mounting device. However, it is also possible to connect the sleeve non-detachably with the mounting device. An arrangement of this type ensures high stability and simple handling of the equipment while carrying out the measurements. It is expedient to form the sleeve essentially of an incombustible material, since the length of the carrier can then be shortened without the sleeve being destroyed by the heat rising from the melt while the receptacle is being dipped into the melt. By way of example, the mounting device can be embodied as a lance or cardboard tube that is common in metallurgy.

It is advantageous that the thermoelement be mounted in the sleeve and connected in a conductive manner with a connecting piece from the sleeve, and that the connecting piece be in contact with signal wires from the mounting device. As a result, the receptacle for taking a molten sample and the thermoelement are combined into one unit which can be removed from the mounting device and exchanged for a new unit after the measurement. The signal wires, which carry the electrical signal from the thermoelement to a plotting unit, can be run inside the mounting device, and are thus protected from damage.

For the realization of a homogenous solidification of the molten mass, it is advantageous that the mounting device be rigidly connected to a vibrator. In accordance with the invention, the object for a procedure for measurement of the liquidus temperature of molten cryolite is achieved by means of the fact that during the measurement of the cooling curve of the molten cryolite in a receptacle, this receptacle vibrates. As a result, a homogenous solidification of the molten cryolite is brought about, starting at the surface of the receptacle. As a result of the vibrating of the molten cryolite during the cooling, undercooling effects in the melt are avoided. The vibration frequency amounts to about 20 to 1000 Hz, preferably 150 to 400 Hz, and the vibration amplitude amounts to about 0.01 to 0.5 mm, preferably 0.08 to 0.15 mm.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF PREFERRED EMBODIMENT

Figure 1:
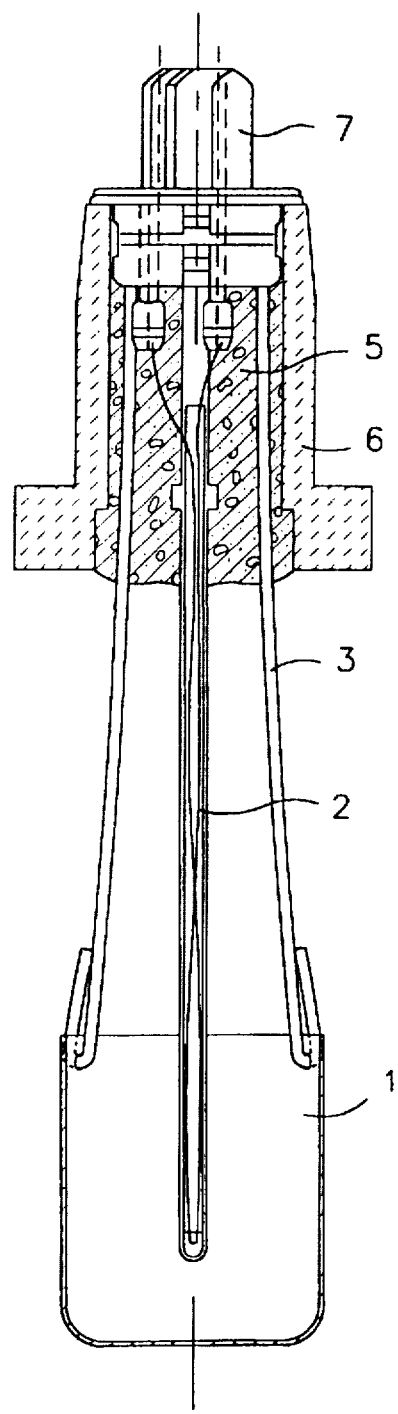
FIG. 1 is a schematic representation of the sensor arrangement according to the invention.

FIG. 1 shows a sensor arrangement in which a thermoelement 2 is arranged in a receptacle 1. The receptacle 1 is made of copper, and has a wall thickness of 0.1 mm. The wires of the thermoelement 2 are arranged inside a small quartz tube, which is closed at its end projecting into the receptacle 1. The small quartz tube has a coating made of metal or a non-oxidic ceramic, for example $TiB_2$, TiN, or BN. This coating can be applied by means of flame spraying, plasma spraying, or vacuum deposition. A dip coating or similar coating process is possible as well.

Figure 2A:
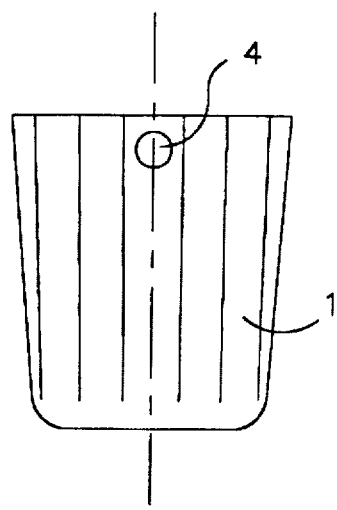
FIG. 2 shows a preferred embodiment of the receptacle.
Figure 2B:
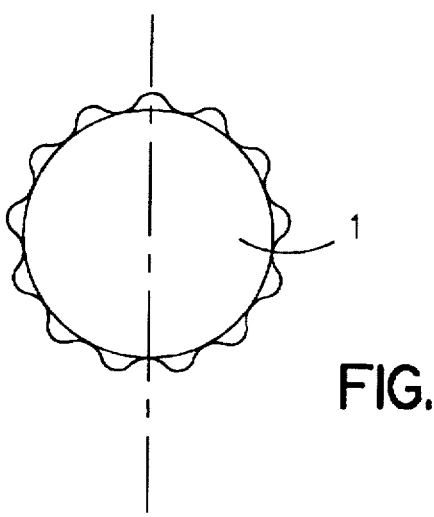

The rotationally symmetrical receptacle 1 is fastened to three carriers 3 formed from metal wires. By way of example, the carriers 3 can be welded to the receptacle 1. Steel with a diameter of 1 mm is used as the material for the carriers 3. The receptacle 1 is shown in detail in FIG. 2. In that regard, FIG. 2a shows a side view of the receptacle 1 with an opening 4 in which one carrier 3 is fastened. FIG. 2b shows a top view of the receptacle 1 in which the corrugated circumferential surface can be clearly seen. Inside, the receptacle 1 exhibits a surface roughness of about 2.5 to 15 μm.

Figure 3:
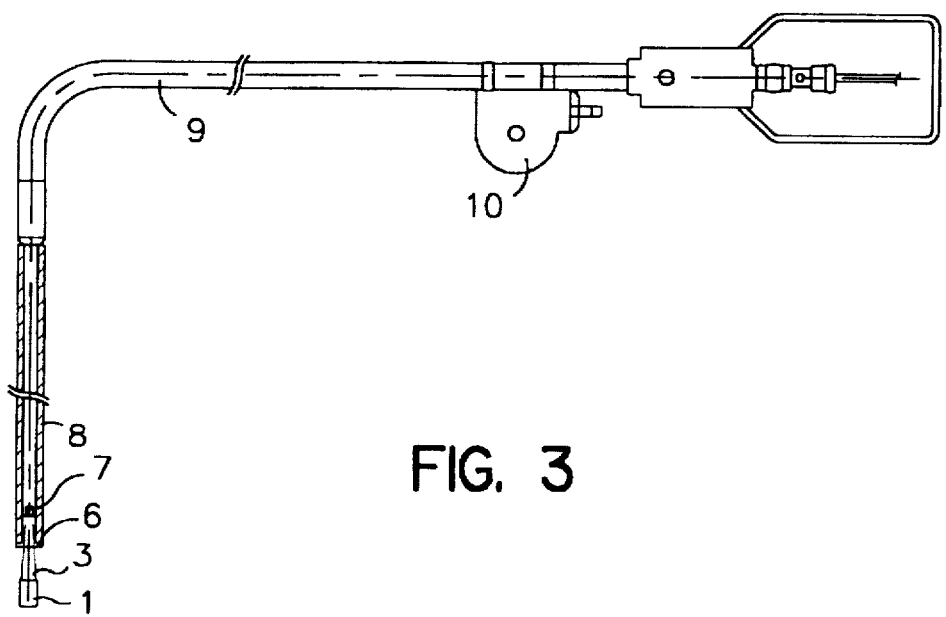
FIG. 3 is a schematic representation of the temperature measuring device, including the mounting device.

The carriers 3 and the thermoelement 2 are fastened by means of cement 5 in a sleeve 6 that is made of a refractory material, for example cordierite. Inside the sleeve 6, the thermowires of the thermoelement 2 are connected with contacts of the connection piece 7. As shown in FIG. 3, the sleeve 6 is arranged in the end of the mounting device 8. There, the contacts of the connection piece 7 are connected in a conductive manner with the signal wires that run through the mounting device 8 and can be connected via the lance 9 to an electronic measuring and plotting device connected behind it. Connected in a rigid manner with the mounting device 8 and the lance 9 is a vibrator 10, which places the receptacle 1 with the molten cryolite to be measured into oscillation during the recording of the cooling curve.

The frequency of the oscillations can be chosen over a very wide range, however it preferably lies between 150 and 400 Hz, in order to avoid undercooling effects on the cooling melt. The amplitude of the oscillations amounts to about 0.08 to 0.15 mm.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

We claim:

1. A sensor arrangement for measuring temperature of a molten cryolite, comprising a cryolite melt receiving receptacle (1) having a high thermal conductivity and low thermal capacity, at least one strip-shaped or wire-shaped carrier (3) for the receptacle, an opening on an upper side of the receptacle, a thermoelement (2) arranged inside the receptacle, the receptacle (1) being made of metal, the thermoelement being arranged in a quartz glass tube having a non-oxidic protective coating, and a vibrator being rigidly connected to the at least one carrier (3) to prevent supercooling of the molten cryolite.

2. The sensor arrangement in accordance with claim 1, where the receptacle (1) has a wall thickness of less than 0.5 mm.

3. The sensor arrangement in accordance with claim 2, wherein the wall thickness is less than 0.2 mm.

4. The sensor arrangement in accordance with claim 1, wherein the receptacle (1) comprises copper.

5. The sensor arrangement in accordance with claim 1, wherein the receptacle (1) has a corrugated surface.

6. The sensor arrangement in accordance with claim 1, wherein the quartz glass tube is closed at one end.

7. The sensor arrangement in accordance with claim 1, wherein the protective coating comprises a temperature resistant metal.

8. The sensor arrangement in accordance with claim 1, wherein the protective coating comprises a non-oxidic ceramic.

9. The sensor arrangement in accordance with claim 1, wherein the thermoelement (2) is arranged approximately centrally of the receptacle (1).

10. The sensor arrangement in accordance with claim 1, wherein the at least one carrier (3) comprises metal wire.

11. The sensor arrangement in accordance with claim 1, wherein an inner surface of the receptacle (1) exhibits a roughness greater than 1.25 μm.

12. The sensor arrangement in accordance with claim 11, wherein the inner surface of the receptacle (1) exhibits a roughness between 2.5 μm and 15 μm.

13. A temperature measuring device with a sensor arrangement in accordance with claim 1, wherein the at least one carrier (3) is mounted at its end facing away from the receptacle (1) in a sleeve (6), and the sleeve (6) is connected to a mounting device (8), the vibrator being rigidly connected to the mounting device.

14. The temperature measuring device in accordance with claim 13, wherein the sleeve (6) comprises an incombustible material.

15. The temperature measuring device in accordance with claim 13, wherein the thermoelement (2) is mounted in the sleeve (6) and is connected in a conductive manner with a connection piece (7) from the sleeve (6), and wherein the connection piece (7) is in contact with signal wires from the mounting device (8).

* * * * *